(12) United States Patent
Gisep et al.

(10) Patent No.: US 9,072,529 B2
(45) Date of Patent: Jul. 7, 2015

(54) CANNULA AND DEVICE FOR LIQUID JET IRRIGATION OF BONE

(75) Inventors: Armando Gisep, Davos Dorf (CH); Philip Kuhn, Davos Platz (CH)

(73) Assignee: AO TECHNOLOGY AG, Chur (CH)

( * ) Notice: Subject to any disclaimer, the term of this patent is extended or adjusted under 35 U.S.C. 154(b) by 865 days.

(21) Appl. No.: 12/812,213

(22) PCT Filed: Jan. 15, 2008

(86) PCT No.: PCT/CH2008/000019
§ 371 (c)(1),
(2), (4) Date: Aug. 27, 2010

(87) PCT Pub. No.: WO2009/089637
PCT Pub. Date: Jul. 23, 2009

(65) Prior Publication Data
US 2010/0318110 A1 Dec. 16, 2010

(51) Int. Cl.
*A61B 17/3203* (2006.01)
*A61B 17/88* (2006.01)
(Continued)

(52) U.S. Cl.
CPC ......... *A61B 17/1644* (2013.01); *A61B 17/8811* (2013.01); *A61B 17/8897* (2013.01);
(Continued)

(58) Field of Classification Search
CPC .............. A61B 17/88; A61B 17/8802; A61B 17/8805; A61B 17/8808; A61B 17/8811; A61B 17/8816; A61B 17/8819; A61B 17/8822; A61B 17/8825; A61B 17/8827; A61B 2017/8813; A61F 2/46; A61F 2/4675; A61F 2002/4677

USPC ...................... 606/92–95, 103–104
See application file for complete search history.

(56) References Cited

U.S. PATENT DOCUMENTS

| 4,583,531 A | 4/1986 | Mattchen |
| 5,084,009 A * | 1/1992 | Mackool ...................... 604/22 |

(Continued)

FOREIGN PATENT DOCUMENTS

| JP | 2005-507698 | 3/2005 |
| WO | 02/02033 A1 | 1/2002 |

(Continued)

OTHER PUBLICATIONS

Majkowski et al.; "Bone Surface Preparation in Cemented Joint Replacement"; British Editorial Society of Bone and Joint Surgery; vol. 75, No. 3; pp. 459-463; May 1993; University of Bristol and Bath, England.

(Continued)

*Primary Examiner* — Christian Sevilla
*Assistant Examiner* — Eric S Gibson
(74) *Attorney, Agent, or Firm* — Rankin, Hill & Clark LLP

(57) ABSTRACT

A cannula (1) comprising a central axis (2), a front end (3) and a through channel (5) coaxial or parallel to said central axis (2) and defining a peripheral wall (12) of said cannula (1), wherein A) said cannula (1) further comprises at least two perforations (8) penetrating said peripheral wall (12) transversely to said central axis (2); B) said through channel (5) is open at said front end (3); and C) the cross section of said through channel (5) has a contraction (6) with a diameter $d_i$ located between the front most of said at least two perforations (8) and said front end (3) which is formed as a guidance for a wire (7). A device (10) for liquid jet irrigation of bone comprising such a cannula (1) and a wire (7).

14 Claims, 1 Drawing Sheet

(51) Int. Cl.
  *A61B 17/16* (2006.01)
  *A61F 2/46* (2006.01)

(52) U.S. Cl.
  CPC ... *A61B2017/1648* (2013.01); *A61B 2217/005* (2013.01); *A61B 2217/007* (2013.01); *A61F 2/4675* (2013.01); *A61F 2002/4677* (2013.01); *A61F 2002/4685* (2013.01)

(56) References Cited

U.S. PATENT DOCUMENTS

| | | | |
|---|---|---|---|
| 5,100,390 A * | 3/1992 | Lubeck et al. | 604/158 |
| 5,505,693 A * | 4/1996 | Mackool | 604/22 |
| 5,919,157 A * | 7/1999 | Strukel | 604/22 |
| 5,976,104 A | 11/1999 | Wolfinbarger, Jr. | |
| 6,770,079 B2 * | 8/2004 | Bhatnagar et al. | 606/94 |
| 6,997,930 B1 * | 2/2006 | Jaggi et al. | 606/93 |
| 7,014,629 B2 * | 3/2006 | Mackool | 604/274 |
| 7,544,196 B2 * | 6/2009 | Bagga et al. | 606/93 |
| 7,601,157 B2 * | 10/2009 | Boyd et al. | 606/92 |
| 8,070,753 B2 * | 12/2011 | Truckai et al. | 606/94 |
| 8,282,594 B2 * | 10/2012 | Perkins | 604/22 |
| 8,821,506 B2 * | 9/2014 | Mitchell | 606/94 |
| 2002/0010472 A1 * | 1/2002 | Kuslich et al. | 606/93 |
| 2002/0156420 A1 | 10/2002 | Anderson et al. | |
| 2005/0070908 A1 * | 3/2005 | Cragg | 606/86 |
| 2006/0122625 A1 | 6/2006 | Truckai et al. | |
| 2007/0260199 A1 * | 11/2007 | Rockley | 604/272 |
| 2008/0300603 A1 * | 12/2008 | Gisep et al. | 606/94 |
| 2009/0105711 A1 * | 4/2009 | Mitchell | 606/92 |

FOREIGN PATENT DOCUMENTS

| | | |
|---|---|---|
| WO | 03/037165 | 5/2003 |
| WO | 2005/053545 A2 | 6/2005 |
| WO | 2006/011152 A2 | 2/2006 |

OTHER PUBLICATIONS

Gisep, A. et al.; "Augmentation of Osteoporotic Bone: Effect of Pulsed Jet-Lavage on Injection Forces, Cement Distribution, and Push-Out Strength of Implants"; Wiley Periodicals, Inc.; Journal of Biomedical Materials Research Part B: Applied Biomaterials; 78B; 2006; pp. 83-88; XP002504636.

* cited by examiner

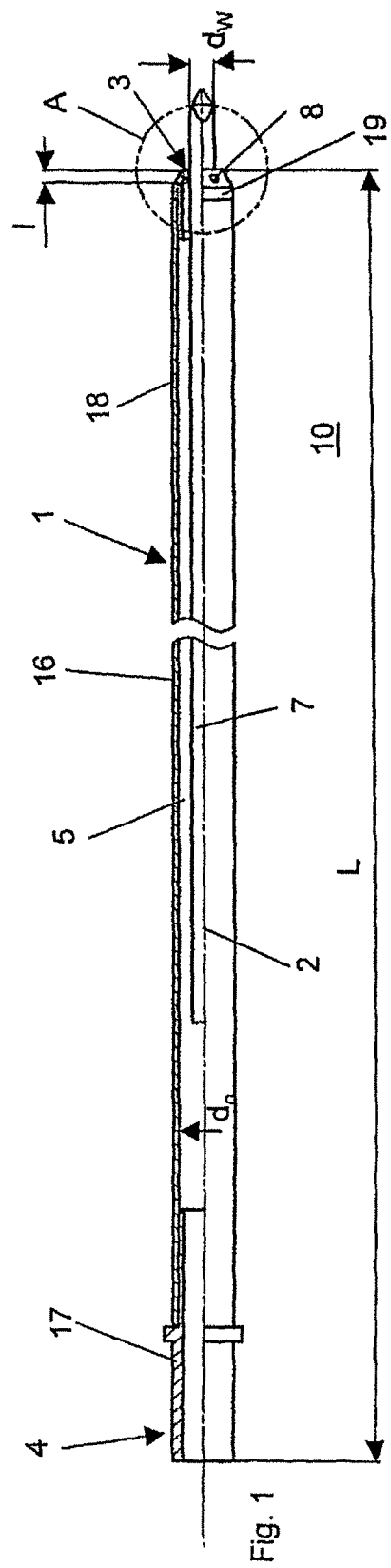
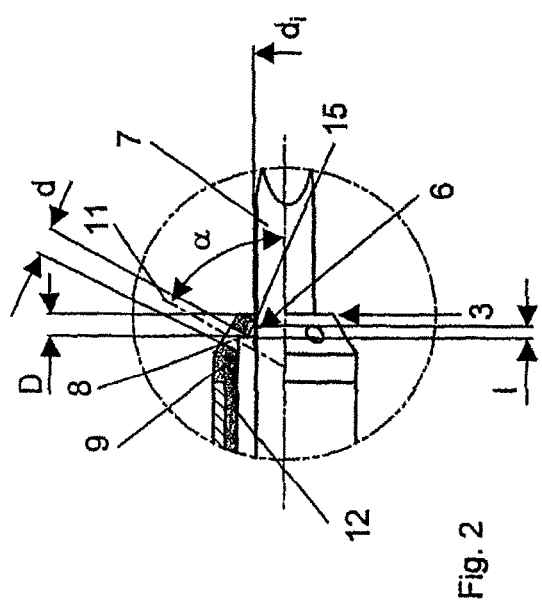

CANNULA AND DEVICE FOR LIQUID JET IRRIGATION OF BONE

FIELD OF THE INVENTION

The invention relates to a cannula for liquid jet irrigation of bone and to a device for liquid jet irrigation of bone comprising such a cannula.

DESCRIPTION OF THE PRIOR ART

In orthopedic surgery implant cut-out after osteosynthesis, e.g. treatment of proximal femur fractures is a major complication often leading to severe and sometimes lethal complications. The rate of implant cut-out was significantly reduced in the past by changing from mostly rigid fixation principles to dynamically active devices such as e.g. the dynamic hip screw. However, the number of failed fixations remains high for comminuted fractures in osteoporotic proximal femurs. Therefore, an urgent need for improvement of implant fixation remains.

Especially in osteoporotic bone the application of a bone cement augmentation of the bone structure around an implant has proven to significantly enhance the performance of the fixation. Specific and controlled augmentation and bone cement distribution around an implant can be achieved with fat and bone marrow removal by irrigation of the bone structure surrounding the implant.

From arthroplasty surgeries e.g. hip joint replacement surgery it is known that irrigation of bone has been carried out for better interdigitation of bone cements with cortical or cancellous bone leading to a significantly better cement penetration.

A study concerning the effects of bone surface preparation on bone cement penetration has been published by: R. S. MAJKOWSKI et al. "Bone surface preparation in cemented joint replacement", The Journal of Bone and Joint Surgery, Vol. 75-B, No. 3, May 1993. This document is related to bone surface preparation in cemented joint replacement. The disclosure particularly concerns the penetration depth of bone cement into the trabecular structure of a bone. The penetration of the applied bone cement into the trabecular structure depends on the extent of marrow removal from the bone interstices.

It has been found that a mean penetration depth of between 4,8 to 7,9 mm can be achieved by use of pressurized liquid jet lavage for a bone surface preparation compared to unprepared bone where a mean penetration depth of 0,2 mm can be achieved. A pressurized liquid jet lavage which is uniformly applied to the bone structure to be prepared results in an equal irrigation of areas with a sparse distribution of trabeculae and areas with a dense distribution of trabeculae.

A hand-held pulsating fluid jet lavage device for delivering a pulsating fluid to a surgical site is known from U.S. Pat. No. 4,583,531 MATTCHEN. Sterilized fluid is supplied from a pump to a rigid tubing terminating at a nozzle which may be pointed at the surgical site to be cleansed. At the axial end of the nozzle the central bore of the rigid tube is terminally closed. The nozzle comprises eight lateral openings connecting the central bore of the tube with the periphery of the nozzle. However, in trauma surgery where Kirschner-wires are crucial instruments for the surgeon as to maintain a reduction of fracture fragments this known device would have the disadvantage that a Kirschner-wire used for the reduction of bone fragments would have be removed during irrigation of e.g. a cavity where an implant is inserted and subsequently inserted again when a cannulated implant, e.g. hip screw or spiral blade is inserted by using the Kirschner-wire as a guide-wire.

SUMMARY OF THE INVENTION

It is an object of the invention to provide a cannula for liquid jet irrigation of bone which allows a precise control of the localization of the irrigation area by means of a guide wire during the irrigation process.

The invention solves the posed problem with a cannula and with a device for liquid jet irrigation of bone comprising such a cannula.

One advantage of the cannula according to the invention is that the surgeon can carry out an irrigation of the bone structure around an in-situ k-wire. The k-wire has not to be removed for the irrigation procedure, hence assuring the later implant position and fracture reduction.

One further advantage of the cannula according to the invention is that—compared to very small diameter cannulas which would have to be used at the side of the pin to irrigate the entire or parts of the bone structure surrounding the cavity—a precise control of the localization of the irrigation area and region is possible.

Another advantage of the cannula according to the invention is that the liquid jet lavage at selected regions only of the bone structure surrounding a previously produced cavity in the bone allows a controlled penetration and distribution of the bone cement in regions of the bone structure where a reinforcement of the trabecular structure is desired. For example, this allows to augment the bone structure at desired regions in order to enhance purchase to an implant (prophylactic and/or traumatic).

In a preferred embodiment each perforation defines an inner orifice in the through channel and said contraction is located between the front most portion of said inner orifice and said front end.

In a further embodiment the at least two perforations are arranged circumferentially at essentially the same angular distance from each other.

In another embodiment the at least two perforations have a hole axis each and all perforations are located in such manner that their hole axes cut said central axis at the same distance from said front end.

In again a further embodiment said through channel has a diameter $d_o$ outside of said contraction and wherein the ratio $d_o/d_I$ of said diameter $d_o$ of said through channel relative to the diameter $d_I$ of said contraction is greater than 1,3; preferably greater than 1,7.

In another embodiment the ratio $d_o/d_I$ is greater than 2, preferably greater than 4.

In a further embodiment said at least two perforations have a hole axis each enclosing an angle α with said central axis measured in a quadrant directed towards the front end, the angle α being smaller than 90°, preferably smaller than 80°. This allows the advantage that the irrigating liquid is applied in the forward direction.

In another embodiment the front most portion of said inner orifice of the front most of said at least two perforations is arranged at a distance D from said front end, D being preferably between 0,5 to 10,0 mm, most preferably between 1,5 to 3,0 mm.

In a further embodiment said contraction of said through channel axially extends over a length I of 0,5 to 3,5 mm, preferably of 1,5 to 2,5 mm over said length L of said cannula.

In another embodiment said diameter $d_I$ of said contraction has a nominal value of 0,6 mm or 0,8 mm or 1,25 mm or 1,6 mm or 1,8 mm or 2,0 mm or 2,5 mm or 2,8 mm or 3,0 mm or 3,2 mm and a permissible variation of between +0,05 mm and +0,5 mm to permit a positive allowance between said contraction and a standard Kirschner-wire. This allows the advantage of a sealing between the through channel of the cannula and the Kirschner-wire simply formed by tolerances of the nominal diameters of the interacting members. Customary Kirschner-wires can be used, e.g. SYNTHES® Kirschner-wires which are available with diameters in a range between 0,6 mm and 3,2 mm such allowing an application to differently sized bones in case of e.g. femoral fractures or fractures at the wrist.

In a further embodiment each of said at least two perforations has a diameter d between 0,1 mm and 3,0 mm, preferably between 0,3 and 2,0 mm.

In again another embodiment the diameter $d_o$ amounts to $d_i+0,5$ mm $\leq d_o \leq d_i+10$ mm outside of said contraction. Typically the diameters $d_i$ and $d_o$ amount to $d_i=2,5$ mm and $d_o=5$ mm.

In a preferred embodiment of the device according to the invention said contraction has a diameter $d_i$ in a range of $(d_w+0,05$ mm$)\leq d_i \leq (d_w+0,5$ mm$)$, wherein $d_w$ is the diameter of the wire.

A BRIEF DESCRIPTION OF THE DRAWINGS

The preferred embodiment of the invention will be described in the following by way of example and with reference to the accompanying drawings in which:

FIG. 1 illustrates a partial longitudinal section through the preferred embodiment of the device according to the invention; and FIG. 2 illustrates a magnified detail A in FIG. 1.

FIGS. 1 and 2 illustrate an embodiment of the device 10 according to the invention comprising a cannula 1 and a wire 7 with a diameter $d_w$ and a cross-section with an area A orthogonal to the central axis 2 of said cannula 1.

Said cannula 1 comprises a front end 3, a rear end 4 and a through channel 5 coaxially penetrating said cannula between said front end 3 and said rear end 4. In the embodiment illustrated in FIGS. 1 and 2 said cannula 1 includes an adapter 17 located at said rear end 4 allowing to connect a feeding tube or the like (not shown), axially subsequently a tube 18 and a front segment 19 at the front end 3 of said cannula 1. The through channel 5 such defines a peripheral wall 12 of the cannula 1. Further, the cannula 1 comprises N perforations 8 penetrating said peripheral wall 12 transversely to the central axis 2. Each perforation 8 defines an inner orifice in the through channel 5 and an outer orifice in the outer peripheral surface 16 of the cannula 1. Since the through channel 5 is open at said front end 3 the cannula 1 may slide over the wire 7. The cross section of the through channel 5 has a contraction 6 with a diameter $d_i$ located between the front most portions 15 of the inner orifices of the N perforations 8 and said front end 3 which forms a guidance for the wire 7.

The N perforations 8 are arranged circumferentially at the same angular distance from each other such that the hole axes 11 of each pair of perforations 8 enclose an angle of 360°/N. The N perforations 8 are located such that their hole axes 11 cut said central axis 2 at the same distance from said front end 3 and that their hole axes 11 each enclose an angle α of 70° with said central axis 2. The cannula 1 is bevelled at the front end 3 such that the outer orifices of the three perforations 8 are situated on the bevelled surface at the front end 3 of the cannula 1.

Further, the diameter $d_o$ of the through channel 5 outside of the contraction 6 is greater than the diameter $d_i$ of said contraction 6. The diameter $d_i$ of the contraction 6 is dimensioned to permit a positive allowance between said contraction 6 and the wire 7, e.g. a standard Kirschner-wire.

Before using the cannula 1 during an irrigation process a cavity is drilled into a bone whereby the diameter of said cavity is greater than the external diameter of the cannula 1. Thus, during the irrigation process when the cannula 1 is inserted into the cavity in the bone the irrigating liquid together with the removed fat and bone marrow can simply "flow" out of the cavity in the bone. Also vacuum could be used and applied in the proximity of the bone surface. This allows the advantage of a simple design of the device and no necessity of providing the cannula with an additional through channel, i.e. a suction channel. However, the cannula might be provided with a suction channel as an additional embodiment.

The diameter of such a cavity in the bone is ca. 1-10 mm greater than the external diameter of the cannula 1. An embodiment having a diameter-difference less than 1 mm would require a suction of the irrigating liquid together with the removed fat and the bone marrow and would reduce the performance of pulsed liquid jet.

The diameter difference between the diameter $d_w$ of the guiding wire 7 and the diameter $d_o$ of the through channel 5 outside of the contraction 6 of the cannula 1 is in the range between 0.5 mm and 10 mm. A diameter difference less than 0.5 mm would result in a reduced performance (low transport volume of irrigating liquid per time).

The inventive cannula 1 is preferably applied in dynamic hip screw (DHS) surgery and allows the advantage that irrigation might take place after tapping of the thread for the hip screw into the bone.

In various embodiments of the present invention the number of perforations 8 is between 2 and 24 while the diameter d of each perforation 8 is in a range between 0,1 mm and 3,0 mm, preferably between 0,3 mm and 2,0 mm.

What is claimed is:
1. A device for liquid jet irrigation of bone comprising:
a wire with a diameter $d_w$; and
a cannula having a central axis, a front end and a peripheral wall defining a through channel coaxial or parallel to said central axis;
wherein said cannula further comprises at least two perforations penetrating said peripheral wall transversely to said central axis,
wherein each of said at least two perforations has a hole axis,
wherein all perforations penetrating said peripheral wall are located in such a manner that their respective hole axes cut said central axis at a same distance from said front end,
wherein said through channel is open at said front end,
wherein said through channel includes a contraction located between a front most portion of said at least two perforations and said front end, said contraction serving as a guidance for the wire, and
wherein the contraction has a diameter $d_i$ in a range of $(d_w+0.05$ mm$) \leq d_i \leq (d_w+0.5$ mm$)$.
2. The device according to claim 1, wherein each of said at least two perforations defines an inner orifice in the through channel, and wherein said contraction is located between a front most portion of said inner orifice and said front end.
3. The device according to claim 2, wherein the front most portion of said inner orifice is arranged at a distance D from said front end, D being between 0.5 to 10.0 mm.

4. The device according to claim 1, wherein said at least two perforations are arranged circumferentially at essentially the same angular distance from each other.

5. The device according to claim 1, wherein said through channel has a diameter $d_o$ outside of said contraction and wherein the ratio $d_o/d_i$ of said diameter $d_o$ of said through channel relative to the diameter $d_i$ of said contraction is greater than 1.3.

6. The device according to claim 5, wherein the ratio $d_o/d_i$ is greater than 2.

7. The device according to claim 5, wherein the diameter $d_o$ amounts to $d_i+0.5$ mm $d_o \leq d_i+10$ mm outside of said contraction.

8. The device according to claim 1, wherein the respective hole axes of each of said at least two perforations encloses an angle a with said central axis, the angle a being smaller than 90°.

9. The device according to claim 1, wherein said contraction of said through channel axially extends a length l of 0.5 to 3.5 mm.

10. The device according to claim 1, wherein said diameter $d_i$ of said contraction has a nominal value of 0.6 mm or 0.8 mm or 1.25 mm or 1.6 mm or 1.8 mm or 2.0 mm or 2.5 mm or 2.8 mm or 3.0 mm or 3.2 mm and a permissible variation of between +0.05 mm and +0.5 mm to permit a positive allowance between said contraction and the wire, the wire being a standard Kirschner-wire.

11. The device according to claim 1, wherein each of said at least two perforations has a diameter d between 0.1 mm and 3.0 mm.

12. The device according to claim 1, wherein the diameter $d_i$ defines a clear opening of the contraction.

13. A method of performing a surgical procedure comprising:
providing a device according to claim 1;
drilling a cavity in a bone, wherein a diameter of the cavity is greater than an external diameter of the cannula;
installing the wire through the cavity drilled in the bone;
inserting the cannula into the cavity drilled in the bone with the wire extending through the through channel of the cannula;
flowing a liquid through the through channel of the cannula to
perform liquid jet irrigation of the bone
with the wire extending through the through channel of the cannula.

14. The method according to claim 13, wherein the cannula is used to perform liquid jet irrigation of selected regions only of the bone surrounding the cavity drilled in the bone.

* * * * *

UNITED STATES PATENT AND TRADEMARK OFFICE
CERTIFICATE OF CORRECTION

PATENT NO.        : 9,072,529 B2  
APPLICATION NO.   : 12/812213  
DATED             : July 7, 2015  
INVENTOR(S)       : Gisep et al.

Page 1 of 1

It is certified that error appears in the above-identified patent and that said Letters Patent is hereby corrected as shown below:

In the claims

Column 5, Line 17, Claim 8, Line 3, after each occurrence of angle, delete "a"; and insert --α--.

Signed and Sealed this  
First Day of December, 2015

Michelle K. Lee  
*Director of the United States Patent and Trademark Office*